US00PP17404P3

(12) United States Plant Patent
Luby et al.

(10) Patent No.: US PP17,404 P3
(45) Date of Patent: Feb. 13, 2007

(54) STRAWBERRY PLANT NAMED 'MNUS 138'

(50) Latin Name: *Fragaria×ananassa*
Varietal Denomination: MNUS 138

(75) Inventors: James J. Luby, St. Paul, MN (US); David K. Wildung, Grand Rapids, MN (US); Gene J. Galletta, deceased, late of Laurel, MD (US); by Nada Galletta, legal representative, Raleigh, NC (US); John L. Maas, Huntington, MD (US); John M. Enns, Hyattsville, MD (US)

(73) Assignees: Regents of the University of Minnesota, Minneapolis, MN (US); The United States of America as represented by the Department of Agriculture, Washington, DC (US)

( * ) Notice: Subject to any disclaimer, the term of this patent is extended or adjusted under 35 U.S.C. 154(b) by 171 days.

(21) Appl. No.: 11/099,728

(22) Filed: Apr. 6, 2005

(65) Prior Publication Data

US 2005/0229279 P1 Oct. 13, 2005

Related U.S. Application Data

(60) Provisional application No. 60/560,508, filed on Apr. 8, 2004.

(51) Int. Cl.
*A01H 5/00* (2006.01)

(52) U.S. Cl. ..... Plt./208

(58) Field of Classification Search ..... Plt./208
See application file for complete search history.

*Primary Examiner*—Kent Bell
*Assistant Examiner*—June Hwu
(74) *Attorney, Agent, or Firm*—Penny J. Aguirre

(57) ABSTRACT

A new and distinct cultivar of Junebearing (short day) strawberry plant 'MNUS 138' combining the characteristics of early season ripening, high yield, excellent survival in cold temperatures, resistance to powdery mildew and red steel root rot and moderate resistance to fungal leaf spot and leaf scorch. 'MNUS 138' yields strawberries characterized by moderately firm flesh, a glossy appearance, moderately tough skin, and a pleasing taste with suitable use in pick-your-own production and home gardens.

1 Drawing Sheet

Botanical classification: *Fragaria×ananassa.*
Variety denomination: 'MNUS 138'.

STATEMENT REGARDING FEDERALLY SPONSORED RESEARCH Research for the development of 'MNU 138' was partially funded by USDA-ARS Memorandum of Understanding No. USDA/58/1275-8M-018.

BACKGROUND OF THE INVENTION

'MNUS 138' is a new strawberry cultivar that was raised as a seedling from a controlled cross made between strawberry cultivars 'Seneca' (U.S. Plant Pat. No. 8,991)× 'Allstar' (not patented) in 1983 in Beltsville, Md. 'MNUS 138' was selected at the University of Minnesota North Central Research and Outreach Center in Grand Rapids, Minn. in 1985. 'MNUS 138' was asexually propagated by stolons and planted for trials conducted from 1987 to 1990 at the University of Minnesota Horticultural Research Center near Excelsior, Minn. and the North Central Research and Outreach Center in Grand Rapids, Minn. It was further propagated by stolons and planted for evaluation in yield trials that took place from 1997 through 2003 at the Horticultural Research Center, the North Central Research and Outreach Center, the West Central Experiment Research and Outreach Center in Morris, Minn., Michigan State University in East Lansing, Mich., Pennsylvania State University in State College, Pa. and Iowa State University in Ames, Iowa. Asexual reproduction of the new cultivar by stolons has shown that the unique characteristics of 'MNUS 138' are stable and reproduced true to type in successive generations.

BRIEF SUMMARY OF THE INVENTION

'MNUS 138' is a short-day strawberry cultivar bearing fruit that matures in the early portion of the fruiting season in the Midwest United States. It is primarily adapted for growing in colder areas of the Midwest and Northeast United States. 'MNUS 138' is distinct from its antecedents in having an earlier period of fruiting. In trials in East Lansing, Mich. in 2000 and 2001, the mean first harvest date for 'MNUS 138' was 10 days before Allstar and 6 days before Seneca. The mean date on which 50% of the total yield for the season was harvested for 'MNUS 138' was 6 days before Allstar and 3 days before 'Seneca'.

Of the strawberry cultivars currently grown in colder areas of the Midwest and Northeast United States, 'MNUS 138' is most similar to the other relatively cold hardy, early season cultivars 'Annapolis' (not patented), 'Honeoye' (not patented), and 'Sable' (U.S. Patent Pending, Published Application No. 20030046739). 'MNUS 138' has been distinguished from these other cultivars based on the following characteristics determined in tests at the trial locations in Grand Rapids and Excelsior, Minn.

Fruit firmness: 'MNUS 138' exhibits firmer fruit than 'Sable' and 'Honeoye' and similar fruit firmness to 'Annapolis'.

Fruit color: When fully ripened, the skin color of 'MNUS 138' is lighter than that of 'Honeoye' and more similar to fruit of 'Annapolis' and 'Sable'.

Average fruit weight: 'MNUS 138' has larger mean fruit weight than 'Sable' and similar fruit weight to 'Honeoye' and 'Annapolis'.

Pubescence on the peduncle: 'MNUS 138' has divaricate pubescence on the peduncle whereas 'Annapolis' and 'Sable' have appressed pubescence.

Shape of the base of the terminal leaflet: 'MNUS 138' has a terminal leaflet base that is more acute than 'Annapolis' or 'Sable'.

Performance of 'MNUS 138' for yield and average berry weight is comparable to the other early season cultivars 'Annapolis', 'Sable', and 'Honeoye' as exhibited in Table 1.

TABLE 1

Yield and mean berry weight of 'MNUS 138' and early cultivars 'Annapolis', 'Sable', and 'Honeoye' in trials at Grand Rapids, Minn., Morris, Minn., Excelsior, Minn., East Lansing, Mich., Ames, Iowa, and State College, Penn.

| | Grand Rapids | | Morris | | Excelsior | |
|---|---|---|---|---|---|---|
| | 2000 | 2001 | 2000 | 2001 | 2000 | 2001 |
| | Yield (1000 lb/acre) | | | | | |
| 'MNUS 138' | 13.8 | 9.0 | 7.1 | 12.2 | 3.9 | 1.4 |
| 'Annapolis' | 6.9 | 4.4 | 0.8 | 5.9 | 4.0 | 1.5 |
| 'Sable' | 9.3 | 10.8 | 0.7 | 11.5 | 5.1 | 5.3 |
| 'Honeoye' | 7.7 | 9.9 | 5.1 | 14.1 | 3.9 | 7.1 |
| LSD (5%) | 6.2 | 8.8 | 4.4 | 6.2 | 2.1 | 2.5 |
| | Berry weight (g) | | | | | |
| 'MNUS 138' | 14.0 | 11.9 | 10.4 | 12.4 | 11.5 | 11.2 |
| 'Annapolis' | 12.4 | 12.8 | 5.8 | 10.7 | 12.2 | 7.6 |
| 'Sable' | 10.5 | 8.5 | 7.4 | 8.4 | 10.0 | 9.1 |
| 'Honeoye' | 12.0 | 11.9 | 10.0 | 11.0 | 13.4 | 9.8 |
| LSD (5%) | 3.0 | 4.0 | 2.3 | 2.3 | 1.8 | 2.1 |

| | East Lansing | | Ames | | State College |
|---|---|---|---|---|---|
| | 2000 | 2001 | 2000 | 2001 | 2003 |
| | Yield (1000 lb/acre) | | | | |
| 'MNUS 138' | 15.1 | 2.8 | 48.3 | 23.9 | 19.6 |
| 'Annapolis' | 9.3 | 3.7 | 9.6 | 30.1 | NA |
| 'Sable' | 11.3 | 6.7 | 15.0 | 25.9 | 16.4 |
| 'Honeoye' | 19.2 | 6.3 | 21.3 | 28.0 | 20.8 |
| LSD (5%) | 4.1 | 6.0 | 11.9 | 9.6 | 6.5 |
| | Berry weight (g) | | | | |
| 'MNUS 138' | 14.9 | 9.8 | 13.3 | 12.7 | 12.1 |
| 'Annapolis' | 11.5 | 9.7 | 11.3 | 11.3 | NA |
| 'Sable' | 10.5 | 10.6 | 8.9 | 9.2 | 11.2 |
| 'Honeoye' | 13.2 | 9.1 | 13.6 | 13.1 | 11.4 |
| LSD (5%) | 1.1 | 1.3 | 5.6 | 3.7 | 1.0 |

'MNUS 138' is moderately resistant to fungal leaf spot (*Mycosphaerella fragariae* Tul.); comparable to 'Annapolis' and 'Sable' and more resistant than 'Honeoye'. 'MNUS 138' exhibits resistance to powdery mildew (*Sphaerotheca macularis* Walls ex Fr.); similar to 'Honeoye' and more resistant than 'Annapolis' and 'Sable'. 'MNUS 138' is moderately resistant to leaf scorch (*Diplocarpon earliana* Ell. and Ev.) and similar to 'Annapolis', 'Honeoye', and 'Sable'. The original plant of 'MNUS 138' was resistant to red stele root rot when screened with a five-race composite of *Phytophthora fragariae* C. J. Hickman var. *fragariae* as a young seedling in the greenhouse in Beltsville, Md. in the winter of 1983–1984.

The berries of 'MNUS 138' have an attractive interior and exterior color and gloss. They are moderately firm, have a moderately tough skin, and have a pleasing flavor that should make the variety useful for commercial pick-your-own strawberry production and home gardens.

BRIEF DESCRIPTION OF THE DRAWING

The accompanying color photograph shows typical fruit and a stolon tip of 'MNUS 138' grown under standard field conditions at Grand Rapids, Minn. The photograph depicts color features as true as is reasonably possible. The color values cited in the detailed botanical description accurately describe the new strawberry.

DETAILED BOTANICAL DESCRIPTION

The botanical data describing 'MNUS 138' was collected at the University of Minnesota Horticultural Research Center in Excelsior, Minn. from plants grown under standard field conditions. The characteristics may vary in detail depending on variations in conditions such as temperature, day-length, light intensity, soil types, and water and fertility levels as 'MNUS 138' was not tested under all possible environmental conditions. The color determination is in accordance with the 1995 R.H.S. Colour Chart of The Royal Horticultural Society, London, England, except where general color terms of ordinary dictionary significance are used.

Inflorescence:

*Average time of flowering.*—First flowers May 21st in Excelsior, Minn.

*Flower position relative to foliage.*—Inflorescence beneath to level with foliage at bloom.

*Diameter of calyx relative to corolla on secondary flowers.*—Calyx is smaller.

*Diameter of inner calyx relative to outer on secondary flowers.*—Equal or slightly larger.

*Spacing of petals.*—Usually not touching.

*Petal color (upper surface).*—155B.

*Sex type.*—Perfect.

*Size of secondary flowers.*—

| | Mean | St. dev. | Range |
|---|---|---|---|
| Calyx diam (mm) | 19.8 | 2.3 | (15–22) |
| Corolla diam (mm) | 27.0 | 4.1 | (23–34) |
| Petal number | 5.1 | 0.4 | (5–6) |
| Petal length (mm) | 10.6 | 1.1 | (9–12) |
| Petal width (mm) | 10.6 | 1.2 | (9–12) |
| Petal length/width ratio | 1.00 | 0.05 | (0.90–1.11) |
| Stamen number | 21 | | (19–24) |
| Stamen length (mm) | 2.5 | | (2.1–2.7) |
| Pistil number | 141 | | (134–148) |
| Pistil length (mm) | 1.1 | | (0.7–1.3) |

*Anther color at anthesis.*—21B.

*Filament color at anthesis.*—150B.

*Pistil color at anthesis.*—151C.

*Pollen color.*—15C.

Fruiting truss characteristics:

*Attitude at first picking.*—Prostrate.

*Peduncle pubescence.*—Moderately dense, divaricate.

Fruit characteristics (data from secondary fruit except where noted):

*Fruit length (mm).*—26.1. 1.9 (23–29).

*Fruit width (mm).*—31.7. 3.4 (29–37).

*Fruit length/width ratio.*—0.83. 0.054 (0.72–0.87).

*Predominant shape.*—Ovoid.

*Difference in shape — primary to secondary.*—Primary more wedge-shaped and secondary more conic-shaped.

*Width of band without achenes on neck of berry.*—Medium (11–12 mm).

*Surface texture.*—Slightly uneven.

*Insertion of calyx.*—Calyx slightly raised.

*Pose of calyx segments.*—Reflexed.

*Size of calyx relative to fruit diam.*—Calyx similar or slightly smaller than fruit.

*Adherence of calyx.*—Strong.

*Glossiness.*—Medium.
*External color.*—Lighter areas 45A and darker areas more exposed to sunlight 46A.
*Internal color.*—45A in darker areas distal to core and 42A and 42B in lighter areas near core of receptable.
*Evenness of color — skin.*—Even.
*Evenness of color — flesh.*—Lighter near core.
*Fruit acidity.*—Medium to strong.
*Fruit sweetness.*—Medium.
*Achene coloration.*—Yellow green or red where exposed to sunlight.
*Insertion of achenes.*—Slightly inserted.
*Seed color on ripe fruit.*—151C.
*Seed length (mm).*—1.2.
*Seed width (mm).*—0.5.

Plant characteristics:
*Plant habit.*—Flat-globose.
*Bearing habit.*—Junebearing (short day).
*Season of harvest.*—Early.
*Hardiness.*—USDA Zone 3b to 5 based on testing in Minnesota, Iowa, and Michigan.

Stolon characteristics:
*Anthocyanin coloration.*—46A and 50C.
*Stolon coloration.*—144B.
*Pubescence.*—Moderately dense, divaricate.
*Stolon length.*—Mean 53 cm, range 35–70 cm.

Leaf characteristics:

| | Mean | St. dev. | Range |
|---|---|---|---|
| Terminal leaflet length (mm) | 43.8 | 3.4 | (40–48) |
| Terminal leaflet width (mm) | 34.7 | 2.7 | (31–38) |

-continued

| | Mean | St. dev. | Range |
|---|---|---|---|
| Terminal leaflet length/width ratio | 1.3 | 0.1 | (1.05–1.37) |
| Number of teeth on terminal leaflet | 19.3 | 2.6 | (17–24) |
| Petiole length (mm) | 78.3 | 14.8 | (62–96) |
| Stipule length (mm) | 18.5 | 2.3 | (15–21) |
| | | 1.2 | (6–9) |

*Terminal leaflet margin profile.*—Flat to revolute.
*Terminal leaflet shape of base.*—Mostly acute, some obtuse.
*Terminal leaflet shape of teeth.*—Obtuse to slightly rounded.
*Color of upper side.*—137A.
*Color of under side.*—147B.
*Petiole color.*—146C.
*Bract frequency.*—Not present.
*Stipule anthocyanin coloration.*—50B.
*Interveinal blistering.*—Medium.
*Glossiness.*—Medium.
*Number leaflets.*—3 on all leaves observed.
*Stipule pubescence.*—Present — sparse.
*Petiole pubescence.*—Present — dense.
*Petiole pose of hairs.*—Divaricate.
*Angle terminal leaflet subtends to petiole.*—30 degrees.
*Pubescence present on upper side of leaflet.*—Yes.

We claim:

1. A new and distinct cultivar of Strawberry plant named 'MNUS 138' as herein illustrated and described.

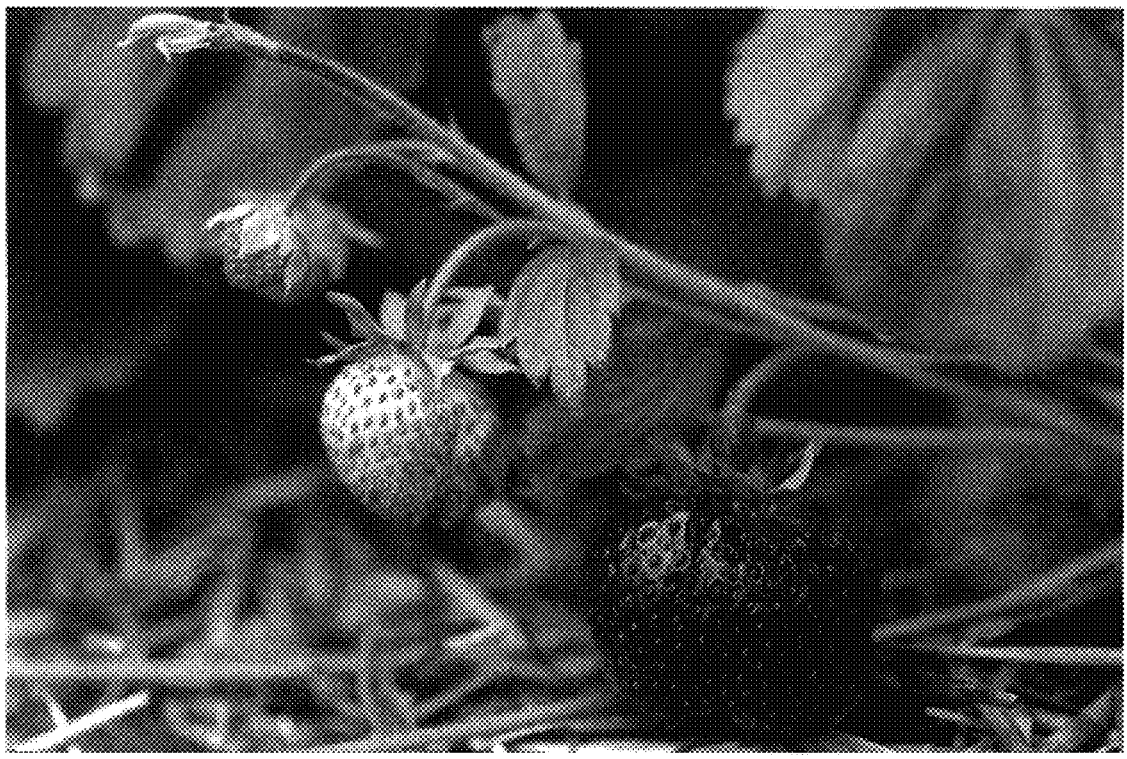

* * * * *